United States Patent
Ross, Jr. et al.

[11] Patent Number: 5,431,659
[45] Date of Patent: Jul. 11, 1995

[54] PNEUMATIC WIRE TENSIONER

[75] Inventors: John D. Ross, Jr., Ovilla; Mikhail L. Samchukov, Coppell; John G. Birch, Dallas, all of Tex.

[73] Assignee: Texas Scottish Rite Hospital for Children, Dallas, Tex.

[21] Appl. No.: 107,943

[22] Filed: Aug. 17, 1993

[51] Int. Cl.⁶ .................. A61B 17/56; B25B 25/00
[52] U.S. Cl. .................. 606/103; 140/123.5; 254/228
[58] Field of Search .......... 606/103, 74, 104; 140/123.5; 254/228

[56] References Cited

U.S. PATENT DOCUMENTS

| | | |
|---|---|---|
| 4,050,464 | 9/1977 | Hall . |
| 4,066,082 | 1/1978 | Arcan . |
| 4,449,429 | 5/1984 | Sauer et al. ............. 254/228 |
| 4,527,554 | 7/1985 | Klein . |
| 4,936,843 | 6/1990 | Sohngen ................. 606/54 |
| 4,966,600 | 10/1990 | Songer et al. ............ 606/103 |
| 5,027,867 | 7/1991 | O'Connor ................ 140/123.5 |
| 5,057,113 | 10/1991 | Mingozzi ............... 606/103 |

FOREIGN PATENT DOCUMENTS 795930  1/1981  U.S.S.R. .......... 140/123.5

*Primary Examiner*—Tamara L. Graysay
*Attorney, Agent, or Firm*—Pravel, Hewitt, Kimball & Krieger

[57] ABSTRACT

The invention relates to a pneumatic wire tensioner device having a piston and a rod slidably mounted within a cylinder. The wire is attached to the rod and the cylinder is placed so as to abut a stationary structure to which the tensioned wire is to be affixed. A pressurized gas is introduced into the cylinder to move the piston away from the structure so as to tension the wire to a predetermined tension.

27 Claims, 3 Drawing Sheets

PNEUMATIC WIRE TENSIONER

BACKGROUND OF THE INVENTION

1. Field of the Invention

This invention relates to a device and method for pneumatically tensioning a wire. More particularly, this device provides a body having a collar which abuts a structure to which the wire is to be connected in the tensioned state, and a piston having a rod which holds the wire. A pressurized gas is used to move the piston from an extended position to a retracted position within the body, which pulls the wire relative to the stationary collar, thus tensioning the wire. Adjustment of the gas pressure provides for a range of possible wire tensions.

2. Description of the Related Art

While the present invention provides for pneumatically tensioning a wire in any of a variety of situations, the device has been particularly designed for tensioning wires used in orthopedic applications, specifically for wires used for fixation of bone to external fixation devices. Wires used in conjunction with external fixation devices are commonly called "Kirschner wires" or "olive wires" and are manufactured with varying diameters.

A number of devices exist for externally fixing bone fractures and correcting bone deformities. One type of such devices, commonly referred to as the "Ilizarov System", utilizes external circular support braces. Generally, circular support braces function by extending a wire(s) through the skin, soft tissue and bone, through both sides of the body part. The extending ends of the wire are secured to a circular member at approximately the diameter of the circular member. Often, two or more circular members are combined to form a cylindrically shaped support brace, each circular member may have a wire extending across the diameter of the circular member which passes through the bone. It is desired to tension the wire to a specific tension to properly install the brace and support any related devices.

There are several known ways in which surgeons presently tension the wires. First, one method provides for a bolt with a radial hole in the shaft, commonly called a "fixation bolt". The wire is placed into the hole and the bolt is turned, thus wrapping the wire around the outer circumference of the bolt shaft to tension the wire. This method does not provide for an accurate tension load, and bending of the wire may result in premature breakage due to stress from the bending.

A number of hand-operated tensioning devices exist which may be used to tension wire or cable in orthopedic applications. Examples of such hand-operated tensioning devices are: U.S. Pat. No. 5,057,113 to Mingozzi, U.S. Pat. No. 4,966,600 to Songer, U.S. Pat. No. 4,936,843 to Sohngen, U.S. Pat. No. 4,066,082 to Arcan, and U.S. Pat. No. 4,050,464 to Hall. However, these devices suffer several disadvantages. First, these hand-operated devices are time consuming to use as they take some time to correctly position, adjust and operate. Also, these devices require the surgeon or attendant to exert a manual force upon the device to tension the wire. This could present difficulties because the surgeon's or attendant's hands may be slippery with bodily fluids or there may be insufficient room to access the device. Further, these devices do not provide for consistent tensioning loads and, hence, may lead to the brace not being properly supported on the patient.

Thus, there exists a need for a easy to operate wire tensioner device which quickly tensions the wire and provides a consistent tension on the wire.

SUMMARY OF THE INVENTION

The invention relates to a pneumatic wire tensioner which has a hollow body having a collar and a piston slidably mounted within the body. The wire is fastened to a rod extending from the piston. The collar is placed so as to abut the external support brace, with the wire passing through the collar and being attached to the rod. A pressurized gas is supplied which moves the piston and rod from a first extended position to a second retracted position which pulls, and hence tensions, the wire relative to the stationary collar and external support brace.

With the present invention, a surgeon installing a circular external brace first securely attaches the wire on one side of the bone to the external brace. Then, on the other side of the bone, the surgeon places the device such that the collar abuts the external brace with the wire being attached to the rod. Then, a pressurized gas is supplied which moves the piston from a first extended position to a second retracted position which pulls and tensions the wire relative to the stationary collar and external brace. After the wire is tensioned, the surgeon securely fastens the wire to the second side of the bone via any convenient means such a bolt.

The present invention provides a pneumatic wire tensioner which quickly, easily, and accurately tensions wires in orthopedic applications.

BRIEF DESCRIPTION OF THE DRAWINGS

A better understanding of the present invention can be obtained when the detailed description of exemplary embodiments set forth below is considered in conjunction with the attached drawings, in which.

DETAILED DESCRIPTION OF EXEMPLARY EMBODIMENTS

Figures 1, 2:
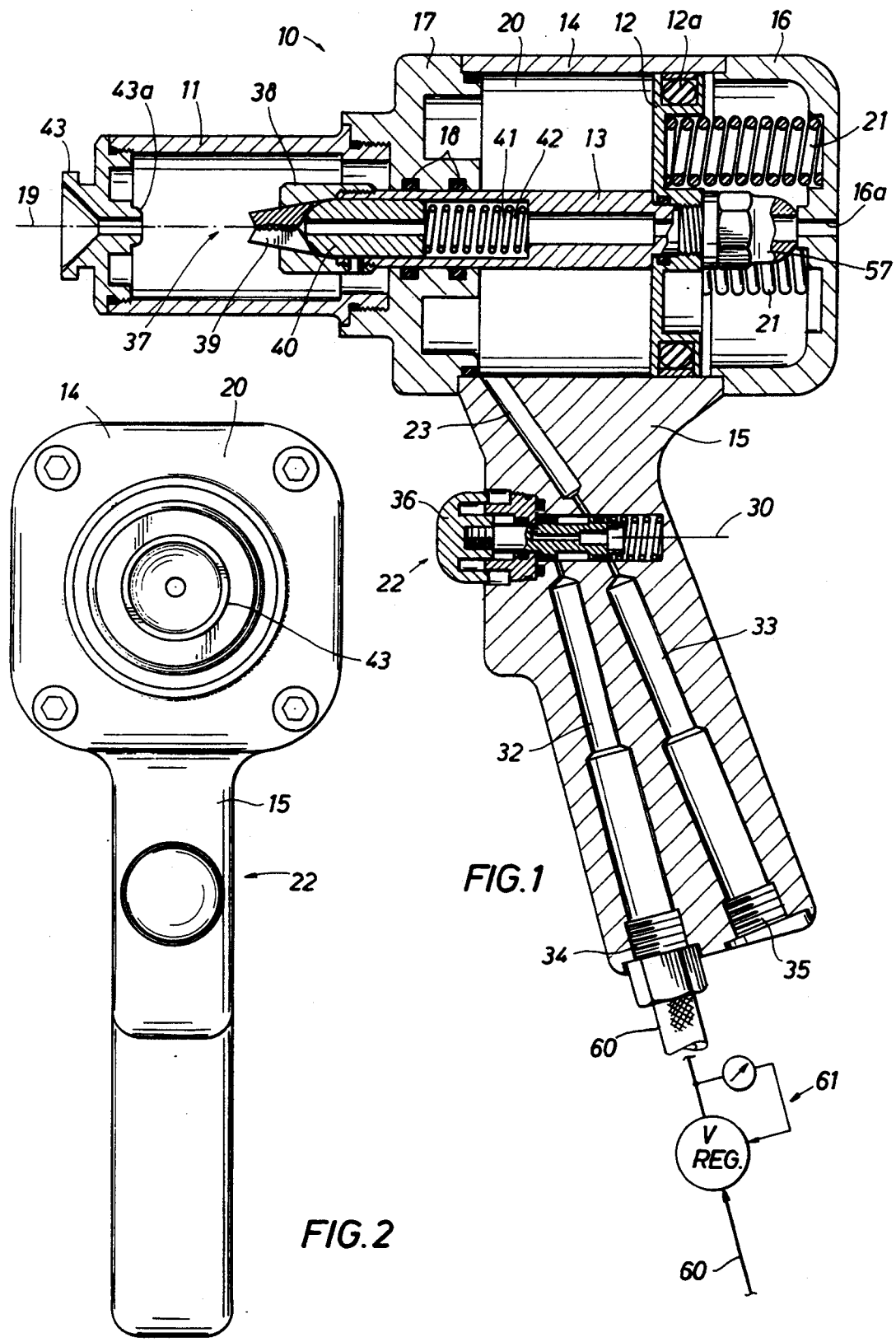
FIG. 1 is a cross-sectional side view of the pneumatic wire tensioner.
FIG. 2 is a front view of the central body portion of the pneumatic wire tensioner.

FIG. 1 shows one embodiment of a pneumatic wire tensioner device 10 which is formed of four major components: (1) a hollow body having a collar 11; (2) a piston 12 and rod 13 combination slidably mounted within the hollow body and collar 11; (3) a mechanism for grasping the wire; and (4) a conduit for supplying pressurized gas to pneumatically move the piston 12 within the hollow body.

In general, the device 10 is placed in use by abutting the collar 11, or an attachment thereto, against an orthopedic structure, such as an external support brace, to which the tensioned wire is to be secured. The wire is placed through the collar 11 and is grasped by a grasping mechanism with the piston 12/rod 13 combination in an extended position. Then, a pressurized gas is utilized to move the piston 12/rod 13 combination from the extended position to a retracted position. This, in effect, pulls and tensions the wire relative to the collar 11 and the orthopedic structure. The wire is then fastened to the orthopedic structure in a tensioned state.

The tensioner body is formed of several integral parts including a central body portion 14, a handle 15, a rear cover 16, a front cover 17, and a collar 11. As shown in FIGS. 1 and 2, the central body portion 14 is hollow and is designed as a cylinder 20 for the piston 12/rod 13 combination. The central body portion 14 and collar 11 has an axis 19. The piston 12 and rod 13 combination slides in the direction of axis 19, with the piston 12 located in the hollow section of the central body portion 14 and the rod 13 moving relative to the collar 11. The piston 12 with ring seals 12a, and a front cover 17 with ring seals 18, form an air-tight cylinder for the pneumatic actuation of piston 12, with the ring seals 18 sealing about the outer circumference of the rod 13, allowing the rod 13 to slide in the direction of the axis 19 while maintaining the seal.

The hollow section of the central body portion 14 i.e., the cylinder 20, between the piston 12 and the rear cover 16 contains at least one spring 21 which serves to push the piston 12/rod 13 combination toward an extended position, i.e., to the left as shown in FIG. 1. Preferably, approximately six springs 21 are located about axis 19. Based upon the position of a trigger mechanism 22 as discussed below, gas either moves through a cylinder channel 23 and enters the cylinder 20 to the left of the piston 12 so as to pneumatically push piston 12 to a retracted position, i.e., to the right as shown in FIG. 1, or the gas exits the cylinder 20 through the cylinder channel 23, which allows the springs 21 to push the piston 12 to the extended position.

Figure 3:
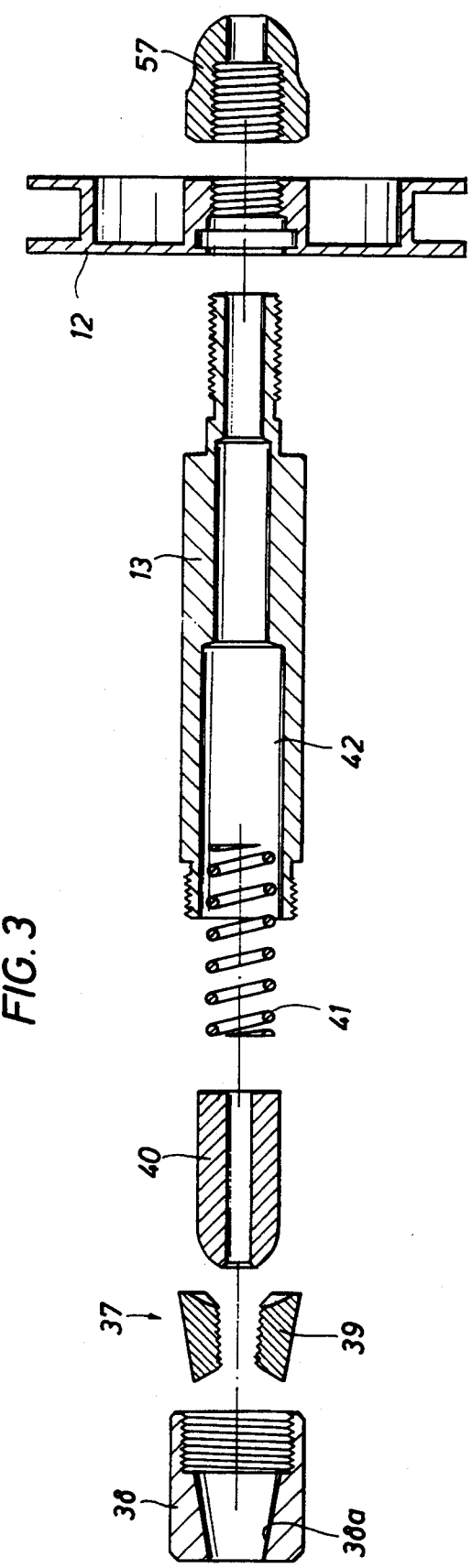
FIG. 3 is an exploded side view of the piston and rod combination and the mechanism for grasping the wire.

As shown in FIGS. 1 and 3, while the piston 12 and rod 13 may be connected in any convenient way, it is preferable to extend the rod 13 through the piston 12 and fasten via a threaded nut 57. The threaded nut 57 also serves to abut against the rear cover 16 to limit the travel of the piston 12 and rod 13 upon retraction.

While the "pneumatic means for moving the piston" and the "means for supplying gas pressure for moving the piston" may consist of any of a variety of ways of routing a pressurized gas from an outside source to the hollow section of the central body portion 14, i.e., to the cylinder 20, so as to move the piston, the preferred embodiment is as discussed below.

Figure 4:
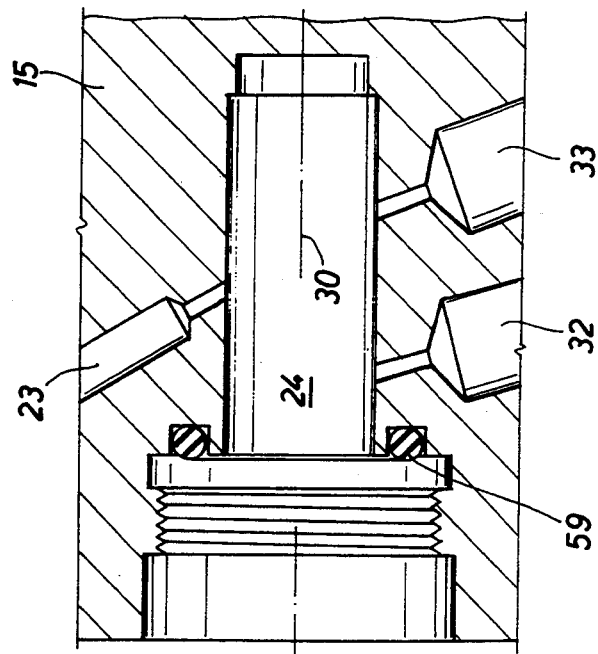
FIG. 4 is an exploded side view of the trigger mechanism and valve.
Figure 4:
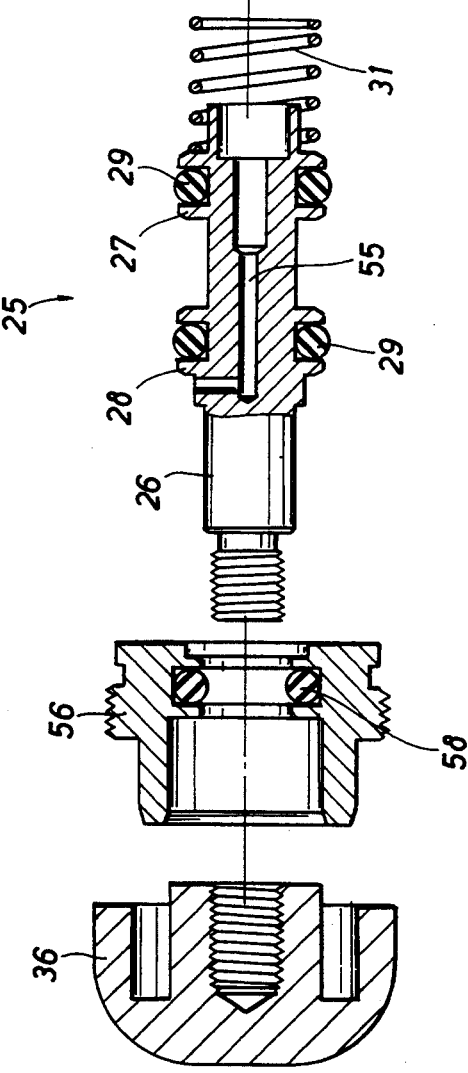

As shown in FIGS. 1 and 4, the handle 15 is designed to accept a trigger mechanism 22 which allows the surgeon or assistant to selectively supply pressurized gas to move the piston 12 to the retracted position or allow the gas to escape from the cylinder 20. When the device 10 is connected to a pressurized gas source and the trigger mechanism 22 is not activated, it is preferred that the pressurized gas is supplied to the cylinder 20 so as to move and hold the piston 12 in the retracted position. When the trigger mechanism 22 is activated, the gas is allowed to escape from the cylinder 20 so as to allow the piston 12 to move to the extended position. Thus, prior to being placed in use, the piston 12/rod 13 is in the retracted position and upon activation of the trigger mechanism 22, the piston 12/rod 13 moves to the extended position. While the device 10 may operate with the reverse operation of the trigger mechanism 22, i.e., activation of the trigger mechanism 22 supplies gas to move the piston 12 to the retracted position, the above noted operation is preferred as it allows the surgeon or assistant to activate the trigger mechanism 22 to apply the device 10 and thereafter, the device 10 continues to tension the wire without further activating of the trigger mechanism 22. This allows the surgeon or assistant to conduct other activities, such as securing the wire to the brace.

The handle 15 has a cavity 24 which is designed to accept valve spool assembly 25. The valve spool assembly 25 has a valve spool shaft 26 and two perpendicular plates; a back plate 27 and a front plate 28. While a variety of valves may perform satisfactorily, the preferred valve is a miniature, normally open, 3-way ported-exhaust pneumatic valve with momentary push button actuation. The valve spool assembly 25 is designed to slide within the cavity 24 along an axis 30. Ring seals 29, located about the outer circumference of the plates 27, 28, seal the plate 27, 28 relative to the cavity 24. A spring 31 is located within the cavity 24 such that it abuts against the back plate 27 and tends to push the valve spool assembly 25 toward an extended position.

Preferably, a retention bushing 56 is included which limits the forward motion or extension of the valve spool assembly 25. An o-ring seal 58, located within the retention bushing 56 and around valve spool shaft 26, prevents pressured gas from leaking out around the valve spool shaft 26. Another o-ring seal 59 forms a gas tight seal between the retention bushing 56 and the handle 15. The retention bushing 56 is secured in place with a set screw or expansion ring (not shown).

The valve spool assembly 25 is designed such that in the extended position, the sealed space between the back plate 27 and the front plate 28 connects the cylinder channel 23 with an input channel 32. This structure allows a pressurized gas, preferably nitrogen, to enter an input port 34, move through the input channel 32, through the space between the back plate 27 and the front plate 28, through the cylinder channel 23 and into the cylinder 20. Gas pressure is thus supplied to move the piston 12 from an extended position to a retracted position.

When the trigger mechanism 22 is operated so as to slide the valve spool assembly 25 to the retracted position, i.e., to the right as shown in FIGS. 1 and 4, the spring 31 is compressed and the space between the back plate 27 and the front plate 28 connects the cylinder channel 23 with the exhaust channel 33. Gas thus flows from the cylinder 20 through the cylinder channel 23, through the space between the back plate 27 and the front plate 28, through the exhaust channel 33, and exit through an exhaust port 35.

Preferably, the valve spool shaft 26 has an internal passageway 55 for fluidly connecting the chamber formed between the retention bushing 56 and the front plate 28 and the chamber behind the back plate 27. These chambers facilitate sealing off the input channel 32 and exhausting the cylinder 20 when the trigger mechanism 22 is pressed. The passageway 55 insures that gas pressure is always equal on both sides of the valve spool assembly 25 and provides a path for pressurized gas in the chamber between the retention bushing 56 and the front plate 28 to escape to the exhaust channel 33 when the trigger mechanism 22 is released.

When the valve spool assembly 25 is in the retracted position, input channel 32 opens to the space between the front plate 28 and the retention bushing 56 and, via passageway 55, to the space behind back plate 27. In the retracted position, the space behind the back plate 27 no longer connects to the exhaust channel 33 and is therefore a sealed space. Thus, the space in front of the front plate 28 and the space behind the back plate 27 are sealed and prevent the flow of pressurized gas from the input channel 32 into the cylinder channel 23, the exhaust channel 33, or out to the atmosphere at the valve spool assembly 25.

A button or key 36 provides a comfortable interface for finger manipulation of the valve. Preferably, key 36 extends into the handle 15 even in the non-actuated position. This prevents pinching during actuation. The key 36 may be secured to valve spool shaft 26 in any convenient way.

Input port 34 and exhaust port 35 are designed to accept the fittings of flexible hoses 60 as available in medical operating rooms. When gas is vented through the exhaust port 35, it is preferable that this gas be routed away from the sterile area.

In use, a back pressure 61 regulator of any known design is installed in the hose 60 leading to input port 34. The back pressure regulator controls the pressure in the hose 60 to the input port 34 and ultimately controls the pressure of the gas which serves to move the piston 12 from the extended position to the retracted position. A higher back pressure will yield a greater pneumatic force pushing toward the retracted position. A lower back pressure will yield a lower force tending to push the piston 12 toward the retracted position. Thus, the tensioning force exerted on the wire may be controlled by adjusting the pressure of the supply gas to the input port 34.

The tensioning rate and release rate are not critical, but should be smooth so as to prevent a jerk or impulse to the wire. The channels 23, 32, 33 may be designed to limit the flow of gas or flow restriction devices (not shown) may be placed in the channels 23, 32, 33 to achieve this objective.

The key 36, integral with the shaft 26, extends beyond the handle 15. A surgeon or assistant operates the device 10 by simply pushing the key 36 from its extended position to the retracted position such that the pressurized gas is blocked from flowing into the cylinder 20 and the gas in the cylinder 20 is allowed to flow out through exhaust channel 33. This allows the springs 21 to push the piston 12 towards the extended position. When the piston 12 is in the extended position, the grasping mechanism is open so as to receive the wire, and the wire can easily be slipped in to the device 10.

When the surgeon or assistant releases the key 36, the valve spool assembly 25 returns to its extended position allowing pressurized gas to flow into the cylinder 20 so as to move the piston 12 to the retracted position. This allows the grasping mechanism to grasp the wire (as described below) and apply tension to it. The surgeon or assistant can then completely let go of the device 10 and use both hands for other tasks.

When the wire is secured to the brace or other structure and the need for wire tensioning is complete, the surgeon or assistant pushes the key 36 to its retracted position. This releases the gas from cylinder 20 and allows the springs 21 to push the piston 12 to the extended position which opens the grasping mechanism and releases the wire, such that the device 10 may be removed from the wire.

As shown in FIGS. 1 and 3, preferably the "grasping means" is formed of a jaw 37 located within a jaw cap 38. The jaw 37 is formed of individual teeth 39 which are elongated in the direction of the axis 19, generally triangular in cross-sectional area and together form two cup-shaped ends (left and right sides of the jaw 37 as shown). A jaw pusher rod 40 pushes against one cup-shaped end (right side) of the jaw 37. The end of the jaw pusher rod 40 is rounded such that contact with the cup-shaped end of the jaw 37 pushes teeth 39 outward to maintain contact with the tapered internal section 38a of jaw cap 38. The rod 13 includes a mounting cavity 42 which is designed to accept a spring 41, the jaw pusher rod 40 and the teeth 39. Further, the rod 13 is designed to mate with the jaw cap 38 so as to restrain the teeth 39 upon being pushed outward by the jaw pusher rod 40. The teeth 39 preferably have a serrated surface which contacts the wire during use.

The coupling end 43 (discussed below) includes a rounded convex protrusion 43a (see FIG. 1) which interfaces with the cup-shape on the front (left side) of the jaw 37 when the rod 13 is in the fully extended position to force teeth 39 apart so as to receive a wire. As springs 21, which push the rod 13 toward the extended position, are much stronger than spring 41, teeth 39 are pushed back and apart within jaw cap 38 when the rod 13 is in the extended position.

When the trigger mechanism 22 is released (deactivated) such that the rod 13 moves towards the retracted position and away from protrusion 43a, jaw pusher rod 40 pushes jaw 37 such that teeth 39 slide in the tapered internal section 38a of jaw cap 38 and contact the wire. Generally, the spring-loaded jaw pusher rod 40 only causes the teeth 39 to contact the wire. A more significant grasping force comes as the wire is tensioned, as tensioning the wire with contacting teeth 39 tends to pull the teeth 39 more into the tapered section 38a of the jaw cap 38, causing the teeth 39 to more strongly grasp the wire. This allows the wire to be tensioned while maintaining a firm grasp.

After the wire has been grasped, tensioned, and affixed to the structure, the surgeon or assistant activates the trigger mechanism 22 to release the wire. As rod 13 moves towards the extended position, the contact between the teeth 39 and the wire tends to push the jaw 37 out of the tapered internal section 38a of jaw cap 38. This, along with the curved end of jaw pusher rod 40 pushing against the cup-shaped end of jaw 37, tends to open jaw 37 so as to release the wire.

With the grasping means configured as above, the surgeon or assistant need only push the wire into the device 10 along the axis 19. The jaw 37, in combination with the jaw pusher rod 40 and the spring 41, allow the wire to be contacted by the serrated surfaces of the teeth 39 such that when the rod 13 moves toward the retracted position the serrated surfaces will grasp the wire and the wire may be tensioned.

The rod 13 is preferably hollow and the rear cover 16 preferably has a hole 16a along the axis 19 to allow the wire to extend beyond the rear cover 16 such that the device 10 may accept long wires. When a wire is desired to be tensioned, the surgeon or assistant need only depress the key 36, which opens the grasping mechanism, and insert the wire through the tip (discussed below), through the collar 11, through the jaw 37, the hollow portion of rod 13 and the hole 16a in the rear cover 16, as required. The surgeon or assistant need not worry about cutting the wire to a specified length prior to tensioning the wire.

The grasping mechanism described above is preferred as it allows for quick and easy grasping of the wire. It is intended that other mechanisms for grasping the wire, such as pivotal jaws and other fastening methods, be included within the scope of the appended claims.

Figure 5A:
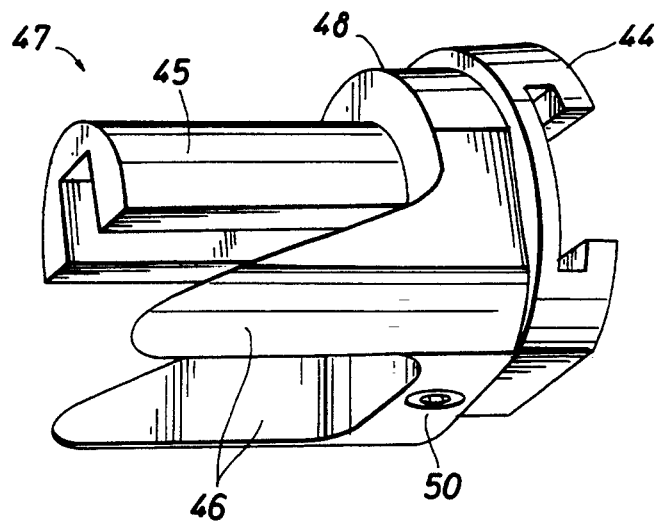
FIG. 5A is an embodiment of the wire tensioner tip referred to as the "ring stabilizer".
Figure 5B:
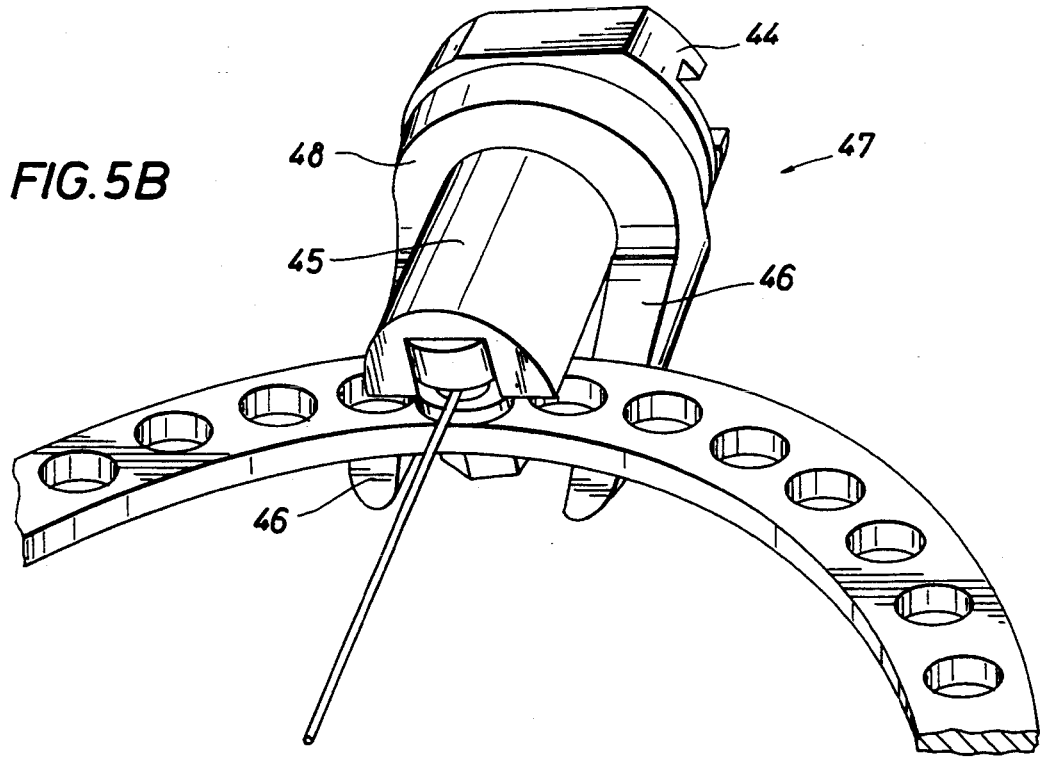
FIG. 5B shows the ring stabilizer tip being used with an Ilizarov type external support brace.

While the device 10 may be used without a tip, preferably, the collar 11 is designed with a coupling end 43 to allow interchangeable use of various tips. Preferably, the coupling end 43 is designed with a conically shaped opening to facilitate the reception of wires at varying angles. Two types of tips are described herein and are referred to as the "ring stabilizer" tip and the "ball-tip". The ring stabilizer tip 47 is shown in FIGS. 5A and 5B. Referring to FIG. 5A, the ring stabilizer tip 47 has a coupling end base portion 44 designed to mate with the coupling end 43 of the collar 11. This coupling connection allows the surgeon or assistant to quickly change the tip to adapt the device 10 to various circumstances. The ring stabilizer tip 47 has a slotted half-cylindrical portion 45 extending from the coupling end base portion 44. Also, the ring stabilizer tip 47 has two ramp portions 46 integral with a collar 48 which allows limited rotation about the slotted half-cylindrical portion 45. A set screw 50 allows the ramp portions 46 to be fixed relative to the slotted half-cylindrical portion 45.

FIG. 5B shows the ring stabilizer tip 47 being used to tighten the wire associated with an Ilizarov ring. As shown, the slotted half-cylindrical portion 45 is designed to mate with the head of the fixation bolt on the top section of the ring. Here, the wire passes through a radial hole in the bolt and continues to the grasping mechanism, i.e., the jaw 37 and associated components. The ring fits snugly between the ramp portion 46 and the slotted half-cylindrical portion 45. Upon releasing the previously depressed key 36, the pneumatic pressure moves the rod 13 and the grasping mechanism such that the wire is tensioned relative to the fixation bolt. Since the head of the fixation bolt is held firmly in place by the slotted half-cylindrical portion 45 such that rotation is prevented, the surgeon or assistant need only tighten the lower nut to secure the wire in a tensioned state to the ring.

Figure 6:
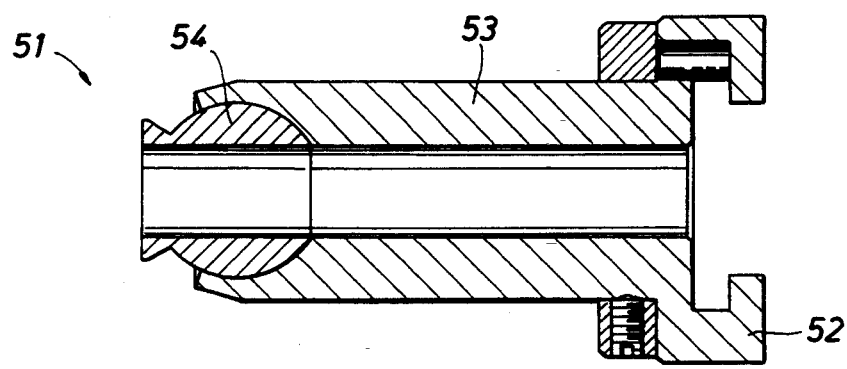
FIG. 6 is an embodiment of the wire tensioner tip referred to as a "ball-tip".

FIG. 6 shows the ball-tip embodiment of the tip member. The ball-tip 51 has a coupling end 52 designed to mate with the coupling end 43 of the collar 11. A hollow shaft 53 extends from the coupling end 52, with the extended end of the shaft 53 designed to accept a hollow ball 54. The hollow ball 54 is placed in its respective position on the shaft 53 and the top of the shaft 53 is crimped to retain the hollow ball 54. This tip embodiment allows for tensioning of wires which are received into the device 10 at various angles. The universal movement of the ball 54 allows the ball-tip 51 to be placed against various structures at an angle such that the wire may be tensioned and affixed to the structure.

While the pneumatic wire tensioner device 10 is specifically designed for use in tensioning wires in orthopedic applications, the device 10 may be used in any wire tensioning application, e.g. industrial or commercial. As discussed above and shown in FIG. 5B, the device 10 is suitable for tensioning wires associated with the Ilizarov type external support brace. In this use, it is desirable to size the surface area of piston 12 such that a predetermined gas pressure will yield a certain tensioning force. The optimum tensioning force varies for each individual application and patient based upon factors such as the size of the bone and the weight of the patient. For example, the preferred tensioning force is generally approximately 130 kg (286 psi). However, large diameter rings are generally less stiff, and, therefore, a lower tensioning force is applied. Also, children's bones and the small bones of a hand or a foot are generally tensioned with a lower force. Further, frequently, the wires are attached to the brace via offset post(s). In this situation, generally a lower tensioning force is applied.

Many variations may be made to the device 10 without deviating from the broader aspects of the invention. For example, while the preferred form of the invention utilizes aluminum as the material for construction, other materials such as stainless steel or plastics can be used. Also, the inventive device may utilize multiple pistons, either in series in parallel, to achieve the tensioning force. Further, the springs 21 may be replaced by a mechanism which provides for the returning of the piston 12/rod 13 to an extended position via the use of gas pressure. Still further, actuation of the pneumatic wire tensioner device may be accomplished remotely, such as with a foot switch, rather than locally, i.e., the trigger mechanism 22.

The pneumatic wire tensioner device 10 solves the problems mentioned above by providing a wire tensioner which quickly, easily, and accurately tensions wires in a variety of applications and is particularly useful in orthopedic applications.

Having described the invention above, various modifications of the techniques, procedures, material and equipment will be apparent to those skilled in the art. It is intended that all such variations within the scope and spirit of the invention be included within the scope of the appended claims.

We claim:

1. An apparatus for pneumatically tensioning an elongated wire with an outside surface and a generally uniform cross section, comprising:
    a hollow body having a collar;
    a piston having a rod with a longitudinal axis, the piston movable within said hollow body, the rod movable within said collar;
    the rod having grasping means conforming to the outside surface and cross section of the wire for receiving the wire longitudinally therethrough and for grasping the outside surface of the wire;
    pneumatic means for moving the piston and the rod from a first extended position to a second retracted position to move the grasping means relative to the collar to tension the wire.

2. The apparatus of claim 1, wherein the pneumatic means for moving the piston comprises a valve for selectively supplying a gas from a supply source to the hollow body so as to exert pressure on the piston to move the piston and the rod from the extended position to the retracted position.

3. The apparatus of claim 2, further comprising a handle integral with the body, said handle containing the valve for selectively supplying a gas from a supply source to the hollow body.

4. The apparatus of claim 3, wherein the handle has an input port and input channel to supply a pressurized gas to the valve and a gas channel to provide gas communication between the valve and the hollow body.

5. The apparatus of claim 1, wherein the pneumatic means for moving the piston comprises a pressure regulator for selectively adjusting the pressure of a supply of pressurized gas so as to selectively adjust the tension on the wire.

6. The apparatus of claim 1, wherein the collar comprises a releasably engagable ring stabilizer tip for securely abutting an orthopedic circular external brace.

7. The apparatus of claim 6, wherein the ring stabilizer tip comprises a slotted half-cylindrical portion for engaging a fixation bolt on a first surface of the external brace and at least one ramp portion for contacting a second surface of the external brace for securely abutting the external brace.

8. The apparatus of claim 1, wherein the collar comprises a releasably engagable ball-tip having a universally movable hollow ball.

9. An apparatus for pneumatically tensioning a wire, comprising:
a hollow body having a collar;
a piston having a rod, the piston movable within said hollow body, the rod movable within said collar;
the rod having grasping means for grasping the wire;
pneumatic means for moving the piston and the rod from a first extended position to a second retracted position to move the grasping means relative to the collar to tension the wire; and
wherein the follow body contains a spring for moving the piston and the rod from the retracted position to the extended position.

10. The apparatus of claim 9, wherein the handle has an exhaust channel from the valve to an exhaust port for relieving gas pressure to allow the piston and rod to move from the retracted position to the extended position.

11. An apparatus for pneumatically tensioning a wire, comprising:
a hollow body having a collar;
a piston having a rod, the piston movable within said hollow body, the rod movable within said collar;
the rod having grasping means for grasping the wire;
pneumatic means for moving the piston and the rod from a first extended position to a second retracted position to move the grasping means relative to the collar to tension the wire; and
wherein the grasping means for grasping the wire comprises a jaw having teeth, said teeth engagable about the wire for exerting a tensioning force.

12. The apparatus of claim 11, wherein said teeth have a serrated surface for contacting the wire.

13. An apparatus for pneumatically tensioning a wire, comprising:
a hollow body having a collar;
a piston having a rod, the piston movable within said hollow body, the rod movable within said collar;
the rod having grasping means for grasping the wire;
pneumatic means for moving the piston and the rod from a first extended position to a second retracted position to move the grasping means relative to the collar to tension the wire; and
wherein the rod is hollow so that the grasping means for grasping the wire may engage a wire which extends beyond the grasping means.

14. An apparatus for pneumatically tensioning a wire with an outside surface and a generally uniform cross section, comprising:
a body having a cylinder, the cylinder having an axis;
a collar integral with the body coaxially located about said axis;
a piston having a rod with a longitudinal axis, the piston slidably mounted within said cylinder to slide in the direction of the axis, the rod slidably mounted within said collar to slide in the direction of the axis;
the rod having grasping means engagable about the wire for receiving the wire longitudinally therethrough and for grasping the outside surface of the wire, and conforming to the cross section of the wire;
means for supplying gas pressure for moving the piston and the rod along the axis from a first extended position to a second retracted position to move the grasping means relative to the collar to tension the wire.

15. The apparatus of claim 14, wherein the means for supplying gas pressure comprises a valve for selectively supplying a gas from a supply source to the cylinder so as to exert pressure on the piston to move the piston and the rod from the extended position to the retracted position.

16. The apparatus of claim 15, further comprising a handle integral with the body, said handle containing the valve for selectively supplying a gas from a supply source to the cylinder.

17. The apparatus of claim 16, wherein the handle has an input port and input channel to supply a pressurized gas to the valve and a gas channel to provide gas communication between the valve and the cylinder.

18. The apparatus of claim 17, wherein the cylinder contains a spring for moving the piston and the rod from the retracted position to the extended position.

19. The apparatus of claim 18, wherein the handle has an exhaust channel from the valve to an exhaust port for relieving gas pressure to allow the piston and rod to move from the retracted position to the extended position.

20. The apparatus of claim 14, wherein the means for supplying gas pressure comprises a pressure regulator for selectively adjusting the pressure of a supply of pressurized gas so as to selectively adjust the tension on the wire.

21. The apparatus of claim 14, wherein the collar comprises a releasably engagable ring stabilizer tip for securely abutting an orthopedic circular external brace.

22. The apparatus of claim 21, wherein the ring stabilizer tip comprises a slotted half-cylindrical portion for engaging a fixation bolt on a first surface of the external brace and at least one ramp portion for contacting a second surface of the external brace for securely abutting the external brace.

23. The apparatus of claim 14, wherein the collar comprises a releasably engagable ball-tip having a universally moveable hollow ball.

24. An apparatus for pneumatically tensioning a wire, comprising:
a body having a cylinder, the cylinder having an axis;
a collar integral with the body coaxially located about said axis;
a piston having a rod, the piston slidably mounted within said cylinder to slide in the direction of the axis, the rod slidably mounted within said collar to slide in the direction of the axis;
the rod having grasping means for grasping the wire;
means for supplying gas pressure for moving the piston and the rod along the axis from a first extended position to a second retracted position to move the grasping means relative to the collar to tension the wire;
wherein the grasping means for grasping the wire comprises a jaw having teeth, said teeth engagable about the wire for exerting a tensioning force.

25. The apparatus of claim 24, wherein said teeth have a serrated surface for contacting the wire.

26. An apparatus for pneumatically tensioning a wire, comprising:

a body having a cylinder, the cylinder having an axis;

a collar integral with the body coaxially located about said axis;

a piston having a rod, the piston slidably mounted within said cylinder to slide in the direction of the axis, the rod slidably mounted within said collar to slide in the direction of the axis;

the rod having grasping means for grasping the wire;

means for supplying gas pressure for moving the piston and the rod along the axis from a first extended position to a second retracted position to move the grasping means relative to the collar to tension the wire;

wherein the rod is hollow so that the grasping means for grasping the wire may engage a wire which extends beyond the grasping means.

27. A method for pneumatically tensioning a wire on an orthopedic circular external brace about a bone, comprising the steps of:

obtaining a device having:

a body having a cylinder, the cylinder having an axis;

a collar integral with the body coaxially located about said axis;

a piston having a rod, the piston slidably mounted within said cylinder to slide in the direction of the axis, the rod slidably mounted within said collar to slide in the direction of the axis;

attaching the wire to the external brace on a first side of the bone;

placing the device on a second side of the bone, opposite to the first side, such that the collar abuts the external brace;

attaching the wire to the rod;

supplying a pressurized gas to the cylinder to move the piston away from the external brace so as to tension the wire; and attaching the wire to the external brace on the second side of the bone.

* * * * *